(12) United States Patent
Allegrini et al.

(10) Patent No.: US 9,751,828 B2
(45) Date of Patent: Sep. 5, 2017

(54) ANTIMUSCARINIC COMPOUND HAVING A LOW CONTENT OF IMPURITIES

(71) Applicant: Dipharma Francis S.r.l., Baranzate-(MI) (IT)

(72) Inventors: Pietro Allegrini, Baranzate (IT); Emanuele Attolino, Baranzate (IT); Renzo Graziosi, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/747,038

(22) Filed: Jun. 23, 2015

(65) Prior Publication Data

US 2016/0031796 A1 Feb. 4, 2016

(30) Foreign Application Priority Data

Jul. 30, 2014 (IT) .............. MI2014A1388

(51) Int. Cl.

| C07C 213/08 | (2006.01) |
|---|---|
| C07C 57/15 | (2006.01) |
| C12P 13/00 | (2006.01) |
| C07C 213/00 | (2006.01) |
| C07C 213/06 | (2006.01) |
| C07C 219/28 | (2006.01) |
| C07C 51/41 | (2006.01) |
| C07C 213/10 | (2006.01) |
| C07C 51/43 | (2006.01) |

(52) U.S. Cl.
CPC ............ C07C 213/08 (2013.01); C07C 51/43 (2013.01); C07C 57/15 (2013.01); C07C 213/06 (2013.01); C07C 213/10 (2013.01); C07C 219/28 (2013.01); C12P 13/005 (2013.01)

(58) Field of Classification Search
CPC ..... C07C 213/08; C07C 51/43; C07C 213/10; C07C 57/15; C07C 219/28; C07C 213/06; C12P 13/005
See application file for complete search history.

(56) References Cited

U.S. PATENT DOCUMENTS

| 6,713,464 B1 | 3/2004 | Meese et al. |
| 8,455,678 B2 | 6/2013 | Artico et al. |
| 8,530,691 B2 | 9/2013 | Mantegazza et al. |
| 8,772,340 B2 | 7/2014 | Artico et al. |

FOREIGN PATENT DOCUMENTS

| EP | 2196452 A1 | 6/2010 | |
| EP | 2251318 A1 | 11/2010 | |
| EP | 21316871 A1 | 5/2011 | |
| EP | 2338871 A1 | 6/2011 | |
| IN | WO 2013035084 A2 * | 3/2013 | ........... C07C 213/00 |
| WO | 2009044278 A1 | 4/2009 | |
| WO | 2009122303 A2 | 10/2009 | |
| WO | 2011029005 A1 | 3/2011 | |
| WO | 2012025941 A2 | 3/2012 | |
| WO | 2013046194 A2 | 4/2013 | |
| WO | 2014006636 A2 | 1/2014 | |

OTHER PUBLICATIONS

Search Report issued by the EPO in Italian Priority Patent Application No. MI2014A001388 filed Jul. 30, 2014, 11 pages.
U.S. Appl. No. 14/293,163, filed Jun. 2, 2014.

* cited by examiner

*Primary Examiner* — Sarah Pihonak
*Assistant Examiner* — Jason A Deck
(74) *Attorney, Agent, or Firm* — Rothwell, Figg, Ernst & Manbeck, P.C.

(57) ABSTRACT

Substantially stable to degradation Fesoterodine fumarate, a process for its preparation and a process for the synthesis of specific degradation impurities of Fesoterodine fumarate are disclosed.

10 Claims, No Drawings

ANTIMUSCARINIC COMPOUND HAVING A LOW CONTENT OF IMPURITIES

FIELD OF THE INVENTION

The invention relates to a process for the preparation of (R)-2-(3-diisopropylamino-1-phenylpropyl)-4-(hydroxymethyl)phenol isobutyrate (Fesoterodine) as fumarate salt, substantially stable as herein defined, that is Fesoterodine fumarate which substantially does not develop degradation impurities; and a method for the preparation of degradation impurities.

STATE OF THE ART

Great efforts have been made over time to prepare pharmaceutical products with a minimum amount of impurities present. Control of impurities is a key parameter for evaluating the efficaciousness of a process and requires the examination of a vast number of options to decide on the reaction conditions and control protocols necessary to ensure that drugs administered to the public are pure and therefore, safer.

The guidelines established by regulatory authorities, for example the Food and Drug Administration (FDA) in the United States, suggest that impurities in pharmaceuticals should be identified if present and if they exceed 0.1% (that is 1,000 ppm). Note that ppm refers to parts per million, therefore 1% is equivalent to 10,000 ppm; 0.1% is equivalent to 1,000 ppm; 0.01% is equivalent to 100 ppm and 0.001% is equivalent to 10 ppm.

Fesoterodine, that is (R)-2-(3-diisopropylamino-1-phenylpropyl)-4-(hydroxymethyl)phenol isobutyrate of formula (I)

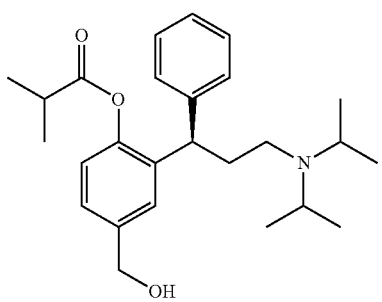

(I)

is a known compound with anti-muscarinic action, used clinically as fumarate salt for treating overactive bladder and in particular urinary incontinence, marketed as TOVIAZ® in the form of tablets containing 4 mg of active ingredient.

U.S. Pat. No. 6,713,464 describes the preparation using various synthesis methods, of which one is set out in the Scheme.

Scheme

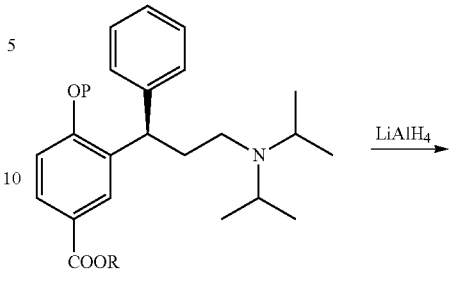

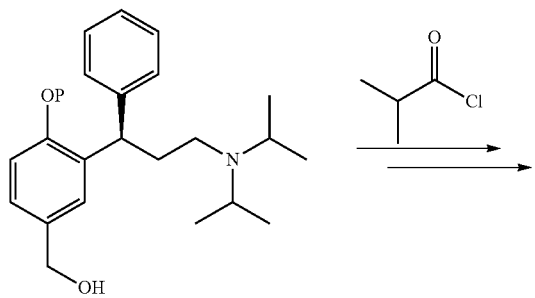

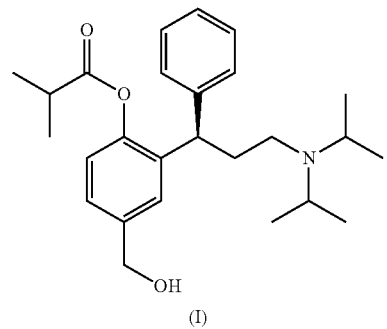

(I)

P = H, protecting group
R = H, alkyl

It has been shown that compounds of formula (II) (tolterodine) and formula (III) (iso-butyrate tolterodine), here below, are typical impurities of Fesoterodine prepared using this synthesis method, generated by the over-reduction of benzyl alcohol using lithium aluminium hydride (LiAlH$_4$).

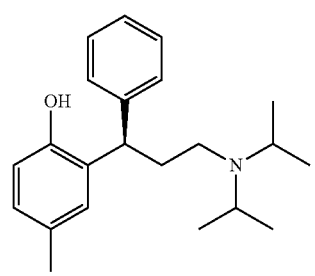

(II)

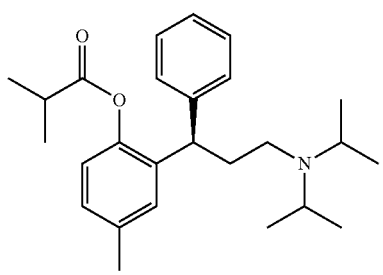
(III)

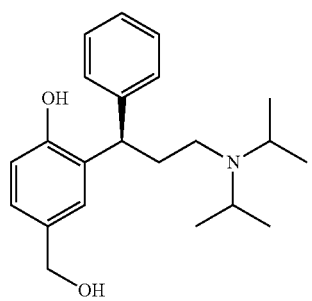
(IV)

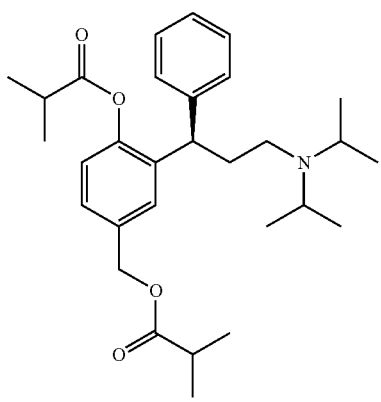
(V)

The impurities in formulas (IV) and (V) are, on the other hand, synthesis impurities found in Fesoterodine caused by incomplete selectivity of the acilating reaction of the intermediate of formula (IV) using isobutyryl chloride as the acilating agent.

The selectivity of the reduction reaction of the carboxylic group with LiAlH$_4$ and that of esterification of phenolic hydroxyl of the compound of formula (IV) with isobutyryl chloride are problems which are resolved, for example, as set out in EP 2 316 817 and EP 2 338 871.

More recently, it has been found that in stability tests, Fesoterodine fumarate salt may degrade leading to the formation of various impurities such as, for example, impurities of formula (VI) and formula of (VII) set out below.

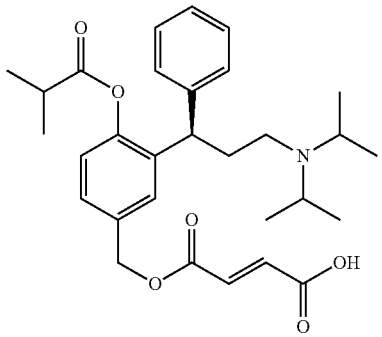
(VI)

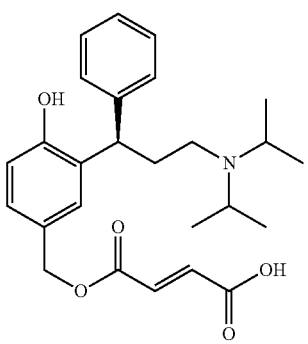
(VII)

It emerges from the studies reported in EP 2 251 318 that in particular, impurity of formula (VI) is generated over time until it exceeds a value of 1% so that Fesoterodine fumarate obtained as disclosed in EP 2 251 318 does not satisfy the permitted ICH limits for known impurities In addition, WO 2013/046194 affirms that during stability tests, other impurities are generated, in particular the two impurities of formulas (VIII) and (IX) with the structures set out below and characterised by the ether bond between the two hydroxyl benzyls.

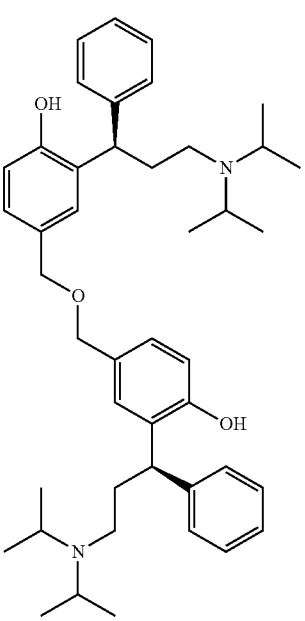
(VIII)

(IX)

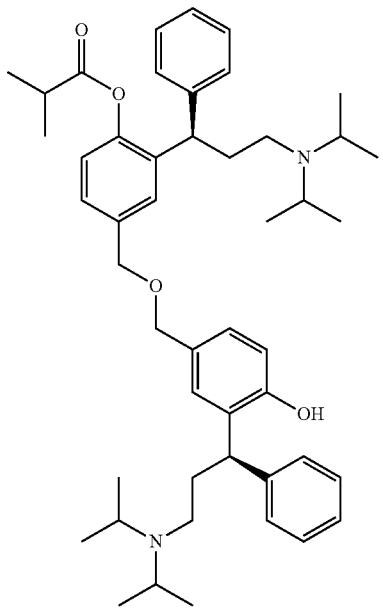

Therefore, there is a need to supply Fesoterodine fumarate which overcomes the disadvantages of the prior art, in particular linked to stability of the fumarate salt, and a process for its preparation.

In addition, in order to analyse the batches put in stability of Fesoterodine fumarate once synthesised, to ascertain that the analytical methods detect the impurities of formulas (VI), (VII), (VIII) and (IX) reported in the aforementioned prior art and to define a HPLC method which allows separating the Fesoterodine peak and quantification of all impurities concerned, new synthesizing methods are required to facilitate synthesis on a scale at least in the order of grams of the impurities of formulas (VI), (VII), (VIII) and (IX), as defined herein.

SUMMARY OF THE INVENTION

A method has been found to prepare Fesoterodine fumarate substantially stable to degradation, Fesoterodine fumarate which substantially does not develop degradation impurities thus obtainable and a process for the preparation of specific degradation impurities of Fesoterodine fumarate of formulas (VI), (VII), (VIII) and (IX), as defined herein.

DETAILED DESCRIPTION OF THE INVENTION

Surprisingly, a process for preparing a substantially stable to degradation Fesoterodine fumarate was found, which is the first subject of the invention, the process comprising:
 the salification of Fesoterodine base with fumaric acid in the presence of a solvent, wherein the molar ratio between Fesoterodine base and fumaric acid is comprised between about 1:0.10 and about 1:0.88, preferably between about 1:0.5 and about 1:0.85;
 the precipitation of Fesoterodine fumarate from the resulting solution;
 the recovery of the solid.

Surprisingly, it was found that unlike all the other methods for synthesis of Fesoterodine fumarate salt known in the prior art, which use a near stoichiometric amount of fumaric acid, the use of a process according to the present invention, which provides the use of a sub-stoichiometric amount of fumaric acid compared with Fesoterodine base, allows obtaining Fesoterodine fumarate which is substantially stable to degradation, therefore which substantially does not develop degradation impurities over time, in particular the impurities of formulas (VI), (VII), (VIII) and (IX), as set out hereunder, (VI)

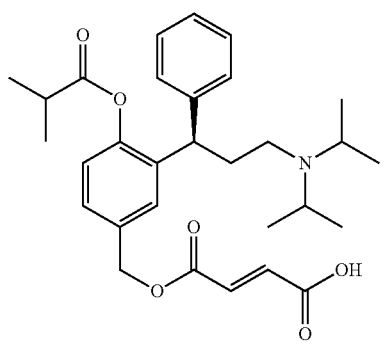

(VII)

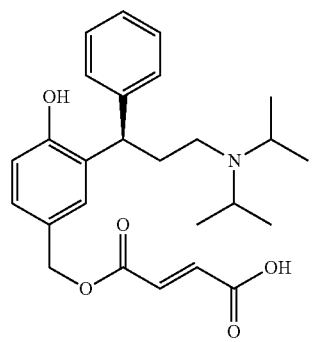

(VIII)

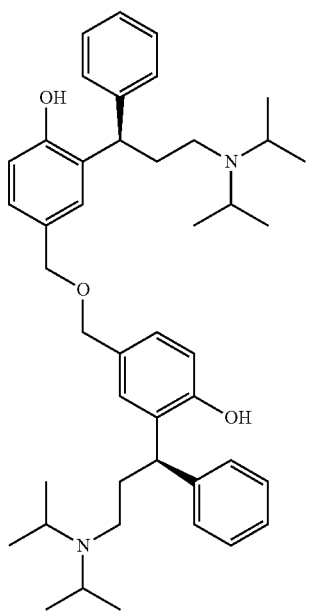

-continued

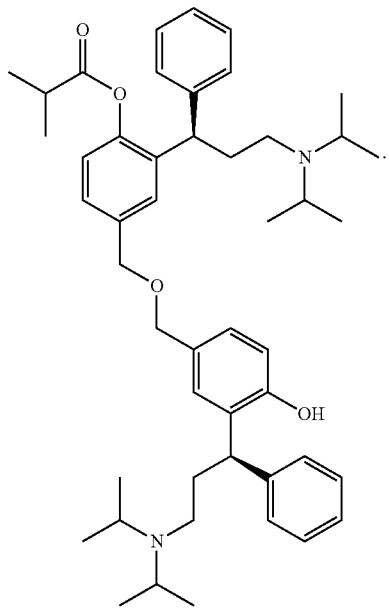

(IX)

Fesoterodine base used as the starting material according to the invention process, can be any Fesoterodine known in the prior art, pure in any solid form or in solution of a solvent, typically organic, for example as obtainable according to U.S. Pat. Nos. 6,713,464, 8,455,678 or 8,530,691.

Fesoterodine base used as the starting material can also be a solution of crude Fesoterodine obtained by the acilation reaction of a compound of formula (IV)

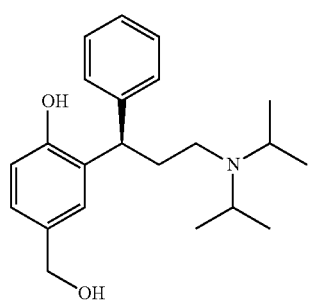

(IV)

with isobutyryl chloride for example as obtained according to U.S. Pat. Nos. 6,713,464, 8,455,678 or 8,530,691. In this case, since Fesoterodine base is not isolated, it is possible to relate the amount of fumaric acid, which must react with Fesoterodine base free in solution, directly to the compound of formula (IV) used in its preparation.

In this case the molar ratio between the compound of formula (IV) used to prepare Fesoterodine base, used in the salification process of the present invention, and the fumaric acid is comprised between about 1:0.10 and about 1:0.85, preferably between about 1:0.4 and about 1:0.80.

A solvent used in the salification reaction can, for example, be selected from the group comprising an aprotic polar solvent, typically dimethylformamide, dimethylacetamide, acetonitrile, dimethyl sulfoxide, a cyclic or acyclic ether, typically tetrahydrofuran or dioxane or methyl tert-butyl ether; a chlorinated solvent, typically dichloromethane; an aprotic apolar solvent typically toluene or hexane, a protic polar solvent such as a straight or branched $C_1$-$C_6$ alkanol in particular methanol, ethanol, isopropanol, n-butanol, tert-butanol, or water; an ester, for example ethyl acetate, isopropyl acetate, butyl acetate, a straight or branched $C_3$-$C_7$ ketone, for example acetone, methy-ethyl-ketone, methyl-isobutyl-ketone; or a mixture of two or more, preferably two or three, of said solvents, most preferably a mixture of acetone and methyl tert-butyl ether.

The precipitation of Fesoterodine fumarate can be facilitated typically by adjusting the temperature of the solution or by adding to the solution a solvent in which Fesoterodine fumarate is insoluble or scarcely soluble, using methods known to the man skilled in the art.

Recovery of solid Fesoterodine fumarate thus obtained can be performed using methods known to the man skilled in the art, for example by filtration in a Buckner filter, by centrifugation or by removal of the solvent, for example at reduced pressure.

Fesoterodine fumarate thus obtained is substantially free from one or more impurities of formulas (VI), (VII), (VIII) or (IX), as defined above, and does not develop said impurities over time.

A further subject of the present invention is therefore a substantially stable to degradation Fesoterodine fumarate and in particular which does not develop one or more impurities of formulas (VI), (VII), (VIII) or (IX), as defined above.

Another subject of this invention is Fesoterodine fumarate which is substantially free of one or more impurities of formulas (VI), (VII), (VIII) or (IX), as defined above.

"Fesoterodine fumarate substantially free of impurities of formulas (VI), (VII) (VIII) or (IX)" or "Fesoterodine fumarate which substantially does not develop degradation impurities, in particular of formulas (VI), (VII) (VIII) or (IX)" means Fesoterodine fumarate, with a total content of one or more impurities of formulas (VI), (VII) (VIII) or (IX) equal to or less than 0.1% calculated as the Area % HPLC or a Fesoterodine fumarate which over time develops one or more impurities of formula (VI), (VII), (VIII) or (IX) in total amount equal to or less than 0.1% calculated as Area % HPLC and is the subject of the present invention.

Preferably Fesoterodine fumarate, according to this invention, has a total content of one or more impurities of formulas (VI), (VII), (VIII) or (IX), typically between about 0.1 and 0.01%, calculated as Area % by HPLC.

Furthermore another subject of the present invention is Fesoterodine fumarate which is substantially stable to degradation as obtainable according to the process of the present invention.

The authors of the present invention, with the aim of evaluating the possible formation of impurities of formulas (VI), (VII), (VIII) or (IX) in some batches of Fesoterodine fumarate put under stability test which can be obtained according to the process of the present invention, conducted a detailed HPLC-MS analysis of the samples of Fesoterodine fumarate obtained according to the above process and sought to synthesise the analytical standards of the four impurities set out above, repeating the prior art processes, as set out below.

More specifically, the authors of the present invention, repeating exactly the synthesis of impurities of formula (VI), as set out in example 4 of EP 2 251 318, after a week of reaction, by analysing the crude at the end of the reaction, identified a compound having the mass of the impurity of formula (VI) but with a content below 5% measured with HPLC, rather than the value of 15% declared in EP 2 251 318 with reference to the process for preparation of the impurity of formula (VI).

Given the small amount of the impurity of formula (VI), this was not isolated by the authors of the invention, who, however, sought to detect in the batches of Fesoterodine fumarate obtained according to the above-mentioned process, the presence of the impurity (VI) of formula, finding a content below 0.1% calculated as HPLC Area %, well below that reported in the stability studies of Fesoterodine fumarate obtained according to the processes of the prior art.

The procedure set out on page 18 of WO 2013/046194 was repeated to synthesize impurities of formulas (VIII) and (IX), but in this case, at the end of the reaction, the residue obtained, analysed by HPLC-MS, did not indicate any structures with the mass of the hypothetical impurities.

The analysed samples have been synthesised using the synthetic process of the present invention which, unlike the prior art processes, makes use of a sub-stoichiometric amount of fumaric acid, as used in the process of the present invention, compared with Fesoterodine base used in the salification process.

It is pointed out that the analysis of the batches of Fesoterodine fumarate, synthesised according to the process disclosed herein, showed contents of impurities of formula (VI), (VII), (VIII) or (IX) so low as to be at the limits of detection of the UV detector of HPLC, contrary to the content of impurities found in the feasibility studies of the prior art and in particular in EP 2 251 318 and WO 2013/046194. In addition, the samples put in stability obtained according to the conditions disclosed in the process of the present invention, surprisingly did not show any increase in the content of the aforementioned impurities over time and were particularly stable, also after 90 days under various temperature and humidity conditions.

Surprisingly, it has been found that unlike all methods for the synthesis of Fesoterodine fumarate salt known in the prior art, that make use of a near stoichiometric amount of fumaric acid compared with the starting Fesoterodine base, the samples of Fesoterodine fumarate analysed by the authors of the present invention obtained according to the foregoing process, have been shown to be unexpectedly stable to degradation.

The Fesoterodine fumarate obtained according to the processes in the present invention had a particle size or $D_{50}$, between about 50 and about 250 μm, calculated using laser light scattering technique. If desired, the value of the "particle size" can be reduced by grinding, micronizing or fine milling.

A further subject of the present invention is a pharmaceutical composition comprising Fesoterodine fumarate substantially stable to degradation, as defined above, as the active ingredient and a pharmaceutically acceptable excipient and/or a carrier.

This pharmaceutical composition can be prepared in a pharmaceutical dosage form according to known methods. The dosage of active ingredient in the composition can be that commonly used clinically for Fesoterodine fumarate, as set out above.

A further subject of this invention is Fesoterodine fumarate substantially stable to degradation, as defined above, for use as a medicament, useful in particular in the treatment of urinary incontinence.

A further subject of the invention is the use of Fesoterodine fumarate substantially stable to degradation, as defined above, for preparing a medicament, useful in particular in the treatment of urinary incontinence.

Therefore, a further subject of the invention is a method of treatment of a mammal, in particular a human being, in need of a drug to treat urinary incontinence, comprising administering to said mammal a therapeutically effective amount of Fesoterodine fumarate substantially stable to degradation, as defined above.

From the standpoint of analysing and quantifying impurities found in samples of Fesoterodine fumarate, for example Fesoterodine fumarate obtained in accordance with the present invention and given that the method set out in the prior art does not allow preparing significant amounts of impurities of formulas (VI), (VII), (VIII) or (IX) to be used as analytical standards, it is made necessary to provide a method for preparation of said impurities.

Surprisingly, a valid process has been found for synthesis of impurities of formula (VI) and/or of formula (VII) or a salt thereof, which overcomes the disadvantages set out above and allows the synthesis of said impurities on a laboratory scale preparation.

A further subject of this invention is therefore a process for preparing a compound of formula (VI) or formula (VII) or a salt thereof, comprising:

the selective enzymatic esterification of benzyl hydroxyls respectively of a compound of formula (I) or formula (IV) or a salt thereof,

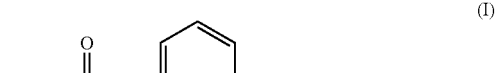

(I)

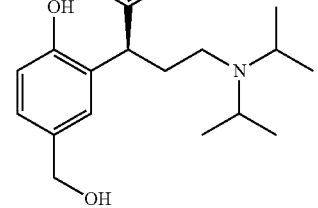

(IV)

with a compound of formula (X)

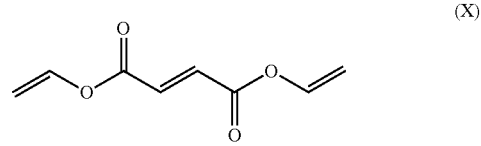

(X)

to obtain respectively a compound of formula (VIa) or of formula (VIIa); and

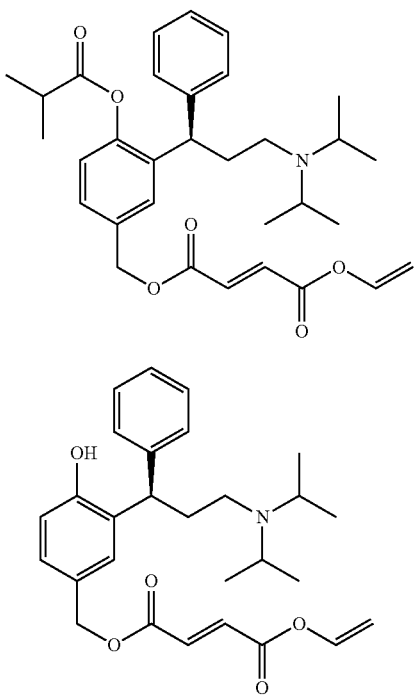

the subsequent selective hydrolysis of the vinyl ester moiety of a compound of formula (VIa) or (VIIa), to obtain respectively, the impurities of formula (VI) or (VII).

Selective enzymatic esterification of benzyl hydroxyls of the compounds in formula (I) and/or formula (IV) with the compound in formula (X) can be performed in a solvent in the presence of *Candida Antarctica* B lipase, for example Cal B Novozyme 435.

A solvent used in the enzymatic esterification reaction can, for example, be selected from the group comprising an aprotic polar solvent, typically dimethylformamide, dimethylacetamide, acetonitrile, dimethyl sulfoxide, a cyclic or acyclic ether, typically tetrahydrofuran or dioxane or methyl tert-butyl ether; a chlorinated solvent, typically dichloromethane; an aprotic apolar solvent typically toluene or hexane, a straight or branched $C_3$-$C_7$ ketone for example acetone, methy-ethyl-ketone, methyl-isobutyl-ketone; or a mixture of two or more, preferably two or three, of said solvents, most preferably the solvent is methyl tert-butyl ether.

Hydrolysis of the vinyl ester moiety in a compound of formula (VIa) or (VIIa) can be performed in the presence of water and an acid and possibly of a solvent.

An acid, used in said hydrolysis reaction, can be a strong protic acid and/or a Lewis acid, for example a strong protic acid can be a mineral acid selected from the group comprising sulfuric acid, hydrochloric acid, perchloric acid or a strong protic acid which can be a strong organic acid selected from the group comprising methanesulfonic acid, para-toluenesulfonic acid, trichloroacetic acid or trifluoroacetic acid, preferably trifluoroacetic acid (TFA). A Lewis acid can be, for example, a salt of a metallic cation, for example a salt of a metal selected from the group comprising boron, aluminium, mercury, zinc and copper, tin, titanium, or a salt of a metal from the lanthanide series selected from the group, comprising lanthanum, cerium, scandium, ytterbium or a mixture of one or more, preferably of two, of the aforementioned acids.

Preferably the salt of a metallic cation is a salt of mercury (II).

In a preferred embodiment of the invention, hydrolysis of the vinyl ester moiety in a compound of formula (VIa) or (VIIa) can be conducted in the presence of water, of trifluoroacetic acid and of a salt of mercury (II), preferably mercury (II) acetate or mercury (II) trifluoroacetate or a mixture thereof.

A process was also found for synthesis of impurities of formula (VIII) or formula (IX) or a salt thereof, which overcomes the disadvantages of the synthesizing processes of the prior art and allows the preparation of said impurities on a laboratory scale preparation.

A subject of this invention is therefore also the preparation of a compound of formula (VIII) or a salt thereof using a process comprising the reaction of a compound of formula (IV) or a salt thereof, with a trifluoromethanesulfonate (triflate) of a rare earth metal, for example a lanthanide or scandium or yttrium in the presence of a solvent as disclosed above. In a preferred version of the invention the triflate salt is preferably Sc(OTf)$_3$, Yb(OTf)$_3$ or La(OTf)$_3$ and the solvent used in the preparation of a compound of formula (VIII) is preferably acetonitrile.

Furthermore, a subject of the present invention is also the preparation of a compound of formula (IX) or a salt thereof using a process comprising the reaction of a compound of formula (IV) or a salt thereof, with Fesoterodine of formula (I) or a salt thereof, in the presence of trifluoromethanesulfonate (triflate) of a rare earth metal, for example a lanthanide or scandium or yttrium in the presence of a solvent as disclosed above. In a preferred embodiment of the invention the triflate salt is preferably Sc(OTf)$_3$, Yb(OTf)$_3$ or La(OTf)$_3$ and the solvent used in the preparation of a compound of formula (IX) is preferably acetonitrile.

A salt of a compound of formula (I), (IV), (VI), (VII), (VIII) or (IX) is one of their pharmaceutically acceptable salts, obtained by reacting a compound of formula (I), (IV), (VI), (VII), (VIII) and (IX) with an acid according to methods well known to a man skilled in the art. Preferably the acid used for salification is hydrochloric acid, hydrobromic acid, tartaric acid, dibenzoyl tartaric acid, fumaric acid.

Once the analytical standards of the impurities of formulas (VI), (VII), (VIII) or (IX) have been obtained using the procedures which are subject of the present invention, it has been proven that the HPLC analytical method used for analysing Fesoterodine of formula (I) as a fumarate salt is capable of identifying said impurities and separating all of them.

Various samples of Fesoterodine fumarate salt of formula (I) have been taken from a batch of product, obtained using the process of the present invention, having a HPLC purity exceeding 99.8% and a content of the impurities of formulas (II), (III), (IV), (V), (VI) or (VII) of less than 0.10%, calculated as HPLC Area %, and completely free of impurities of formula (VIII) and (IX). Some of the samples taken were also micronized to reduce the particle size, both the samples directly taken from the sample batch and the micronized samples have been subjected to stability studies under various temperature and humidity conditions for up to 90 days.

An example of the conditions used in the stability studies were 40° C. with 75% relative humidity and 25° C. with 60% relative humidity.

The HPLC analysis of the samples has not shown the formation of impurities of formula (VIII) and/or (IX) in any of the conditions used and the impurities content of formula (VI) and/or (VII) has resulted less than 0.10%, calculated as HPLC Area %.

A sample of a so synthesised and micronized Fesoterodine fumarate salt, maintained for 3 months at 4° C., has resulted completely unaltered.

The following examples further illustrate the invention:

EXAMPLE 1

Synthesis of Fesoterodine Fumarate of Formula (I)

In a reactor under inert atmosphere at about 20° C., R-(+)-2-(3-diisopropylamino-1-phenylpropyl)-4-hydroxymethyl)phenol of formula (IV) (6.6 kg, 19.35 mol), 5.33 kg of potassium carbonate are suspended in a mixture of toluene (36.7 kg) and ethanol (10.5 kg). The reaction mixture is kept under stirring and cooled to about −5° C. and treated by slow dripping with a solution of isobutyril chloride (2.67 kg, 25.06 mol) in toluene (2.48 kg). After the addition is completed, the reaction mixture is maintained under stirring and heated to 20° C. then treated with water. The phases are separated and the organic phase is repeatedly extracted using aqueous solutions of acetic acid. The combined aqueous phases are washed with toluene, treated with potassium carbonate added up to pH>9, then extracted with methyl tert-butyl-ether (MTBE). The organic phase is treated with acetone and fumaric acid (1.79 kg, 15.43 mol). The mixture is maintained under stirring, then centrifuged and washed with a mixture of MTBE (methyl tert-butyl-ether)/acetone. Fumarate salt of Fesoterodine of formula (I) is obtained with HPLC purity exceeding 99.8% and a content of impurities of formula (II), (III), (IV), (V), (VI) and (VII) of less than 0.10% calculated as Area % HPLC completely free of impurities of formula (VIII) e (IX).

EXAMPLE 2

Synthesis of Divinyl Fumarate

In a 1 liter 4-necked round-bottomed flask equipped with a mechanical stirrer, a thermometer and a condenser, under nitrogen, fumaric acid is added (71 g, 0.15 mol) to a mixture of toluene (220 ml) and vinyl acetate (220 ml). p-Toluenesulfonic acid (1.1 g, 1.47 mmol) and $Hg(CF_3COO)_2$ (1.3 g, 0.75 mmol) are added. The mixture is heated to reflux under vigorous stirring. After 48 hours the reaction mixture is filtered and the clear organic phase is washed with a solution of 10% $K_2CO_3$. The organic phase is dried with $Na_2SO_4$ and concentrated at reduced pressure to produce a residue which is then purified by flash chromatography (hexane:AcOEt:NH3aq=9:1:0.01). Divinyl fumarate (9 g) is obtained, as a white solid, with a yield of 9%.

$^1$H-NMR (300 MHz, CDCl$_3$) δ: 7.38-7.31 (2H, m), 7.97 (2H, s), 5.50-5.06 (2H, m), 4.73-4.70 (2H, m).

EXAMPLE 3

Synthesis of a Compound of Formula (VI)

In a 250 ml 4-necked round-bottomed flask equipped with a mechanical stirrer, a thermometer and a condenser, under nitrogen, the compound of formula (IV) (3 g, 8.8 mmol) and the divinyl fumarate (7.39 g, 44 mmol), as obtained in Example 2, are dissolved in MTBE (i.e. 60 ml of methyl tert-butyl-ether). Cal B Novozyme 435 (3 g) is added. The reaction mixture is left under slow stirring at ambient temperature for 16 hours. The end of reaction mixture containing a compound of formula (VIa) is then filtered and partially concentrated, treated with water (15 ml), acetone to have a single phase, trifluoroacetic acid (3 ml) and catalytic Hg(OTFA)2 (10 mg, 23 μmol). The hydrolysis mixture is kept under stirring at ambient temperature for 6 hours, on completion of which the HPLC/MS analysis shows the full hydrolysis of the compound of formula (VIa). The solution is partially concentrated, diluted with $CH_2Cl_2$ and filtered. The clear organic solution is dried on anhydrous $MgSO_4$, filtered and concentrated to produce a volume of about 70 ml. The suspension is filtered again and the clear solution obtained analysed using $^1$H NMR (internal standard method) presents a titre of impurity of formula (VI) of 2% w/w. Unfortunately, the attempts to concentrate the solution to a residue result in a decomposition of the sample, so the standard solution at 2% is not further concentrated, but used as such in the analysis and preserved at 4° C. to avoid loss of titre.

A rate of the solution is diluted in deuterated chloroform and partially concentrated. The operation is repeated to remove dichloromethane and the solution of the impurity in CDCl$_3$ was directly analysed using NMR.

(APCI) M+1=440.3

$^1$H-NMR (300 MHz, CDCl$_3$) δ: 7.34-7.26 (5H, m), 7.10 (1H, d, J=6.5 Hz), 7.03 (1H, s), 6.86-6.81 (3H, m), 5.07 (2H, s), 4.30 (1H, m), 3.66-3.62 (2H, m), 2.95 (2H, m) 2.61-2.56 (2H, m) 1.35-1.25 (12H, m).

$^{13}$C-NMR (75 MHz, CDCl$_3$) δ: 168.5, 154.6, 141.3, 129.8, 129.7, 129.4, 129.1, 128.1, 127.4, 125.7, 116.7, 69.8, 55.4, 46.8, 42.6, 18.7, 18.6, 17.4, 17.2.

EXAMPLE 4

Synthesis of a Compound of Formula (VII)

In a 250 ml 4-necked round-bottomed flask equipped with a mechanical stirrer, a thermometer and a condenser, Fesoterodine of formula (I) (3.96 g, 9.6 mmol) and divinyl fumarate (8 g, 48.2 mmol) are dissolved in THF (i.e. Tetrahydrofuran 80 ml). Cal B Novozyme 435 (3.96 g) is added. The reaction mixture was maintained under slow stirring at ambient temperature for 2 hours, when analyzed using HPLC-MS the disappearance of Fesoterodine of formula (I) and the presence of the intermediate of formula (VIIa) are shown.

The end of reaction mixture is then filtered and partially concentrated, treated with water (24 ml), acetone to have a single phase, trifluoroacetic acid (TFA) (4.5 ml) and catalytic Hg(OTFA)2 (10 mg, 23.4 μmol). The hydrolysis mixture is maintained under stirring at ambient temperature for 2 hours, then partially concentrated and diluted with AcOEt (150 ml). The solution is dried with MgSO$_4$, filtered and concentrated at reduced pressure to obtain a suspension that is filtered. The clear solution is diluted with toluene and concentrated to obtain an oleous residue that is taken up with MTBE (7 ml). The solid precipitate is filtered and dried. 1.5 g of a compound of formula (VII) are obtained as a white solid with a yield of 30.6%.

(APCI) M+1=510.36

$^1$H-NMR (300 MHz, DMSO-d$_6$) δ: 7.65 (1H, s), 7.41-7.25 (6H, m), 7.14-7.11 (1H, dd, $J_1$=4.8 $J_2$=9 Hz), 6.78 (2H, s), 5.27 (2H, s), 4.19 (1H, m), 3.65 (2H, m), 2.95-2.91 (3H, m), 2.45 (2H, m) 1.33-1.15 (18H, m).

$^{13}$C-NMR (75 MHz, DMSO-d$_6$) δ: 174.9, 165.6, 164.4, 148.2, 142.3, 135.2, 133.6, 132.2, 128.5, 127.8, 127.7, 127.5, 126.7, 123.1, 66.0, 54.0, 45.3, 40.8, 33.3, 31.8, 18.7, 18.5.

EXAMPLE 5

Synthesis of a Compound of Formula (VIII)

In a 25 ml 2-necked round-bottomed flask equipped with a mechanical stirrer, a thermometer and a condenser, under nitrogen. a compound of formula (IV) (1 g, 2.93 mmol) is suspended in CH$_3$CN (5 ml) and the mixture treated with TFA (i.e. 270 μl trifluoracetic acid). The reaction mixture is heated to 60° C., treated with Sc(OTf)$_3$ (28.8 mg, 59.7 μmol) and maintained under stirring at the same temperature for 12 hours.

The mixture is then cooled to about 20-25° C., treated with a saturated solution of NaHCO$_3$ (10 ml) and extracted with ethyl acetate. The combined organic phases are dried with Na$_2$SO$_4$, filtered and concentrated at reduced pressure. A residue is obtained and purified by chromatography on silica C-18 (water+1% of TFA/methanol). After evaporation of the fractions, 200 mg of the desired product are obtained as an oil which is dissolved in isopropanol (6 ml) and treated with (D)-dibenzoyl tartaric acid (107 mg). The precipitated salt is filtered and 270 mg of impurity of formula (VIII) are obtained as a salt of (D)-dibenzoyl tartrate.

(APCI) M+1=665.51

$^1$H-NMR (300 MHz, DMSO-d6+D$_2$O) δ 9.45 (2H, bs), 8.01 (4H, d, J=7.8 Hz), 7.56 (2H, t, J=6.9 Hz), 7.41-7.32 (6H, m), 7.18-7.08 (10H, m), 6.95 (2H, d, J=7.8 Hz), 6.76 (2H, 8.4 Hz), 5.74 (2H, s), 4.35 (4H, s), 4.18 (2H, t. J=7.5 Hz), 3.34 (4H, m), 2.79 (2H, m), 2.62-2.29 (6H, m), 1.03 (12H, d, J=6 Hz).

$^{13}$C-NMR (75 MHz, CDCl$_3$) δ: 169.4, 165.7, 154.2, 143.9, 133.2, 130.8, 129.8, 129.7, 129.4, 128.7, 128.5, 128.2, 127.8, 127.4, 126.4, 115.2, 75.3, 71.8, 53.7, 45.5, 41.0, 32.2, 17.5.

EXAMPLE 6

Synthesis of a Compound of Formula (IX)

In a 250 ml 4-necked round-bottomed flask equipped with a mechanical stirrer, a thermometer and a condenser, under nitrogen, the compound of formula (IV) (4.15 g, 12.2 mmol) and Fesoterodine of formula (I) (5 g, 12.2 mmol) are suspended in CH$_3$CN (50 ml). The suspension is treated with trifluoroacetic acid (2.2 ml) heated to 60° C. and Sc(OTf)$_3$ (120 mg, 0.24 mmol) is added. The reaction mixture is maintained under stirring at 60° C. for 12 hours, then cooled to about 20-25° C. and treated with a saturated solution of NaHCO$_3$ (60 ml). The mixture is repeatedly extracted with ethyl acetate and the combined organic phases are dried with Na$_2$SO$_4$, filtered and concentrated under reduced pressure. A residue is obtained that is purified by chromatography on silica C-18 (water+1% of TFA/methanol). After evaporation of the fractions, 1.03 g of impurity of formula (IX) is obtained as an oil, dissolved in a mixture of acetone (2 ml) and MTBE (2 ml) and treated with fumaric acid (163 mg). The suspension is left under stirring at about 20° C. for 12 hours and the suspended solid is filtered. 900 mg of impurity of formula (IX) are obtained as solid crystalline fumarate salt.

(APCI) M+1=735.63

$^1$H-NMR (300 MHz, DMSO-d6+D$_2$O) δ 7.40 (1H, s), 7.27-7.14 (12 H, m), 6.99-6.94 (2H, m), 6.79 (1H, d, J=7.8 Hz), 6.49 (2H, m), 4.41-4.28 (5H, m), 4.09 (1H, m), 3.40-3.25 (4H, m), 2.85 (1H, m), 2.70 (2H, m), 2.57 (2H, m), 2.27 (4H, m), 1.26-1.20 (6H, m), 1.09-0.99 (24H, m).

$^{13}$C-NMR (75 MHz, CDCl$_3$) δ: 174.9, 168.2, 154.4, 147.7, 144.2, 143.3, 136.6, 135.8, 135.5, 129.8, 128.8, 128.7, 128.5, 128.0, 127.8, 127.7, 127.4, 127.3, 126.8, 126.6, 126.3, 71.8, 70.8, 52.6, 51.5, 45.2, 44.3, 41.1, 33.6, 19.0, 18.8, 18.7, 18.3, 18.2.

The invention claimed is:

1. A process for the preparation of a substantially stable to degradation Fesoterodine fumarate, comprising:
    salifying Fesoterodine base with fumaric acid in the presence of a solvent wherein the molar ratio between Fesoterodine base and fumaric acid is comprised between about 1:0.10 and about 1:0.88;
    precipitating Fesoterodine fumarate from the resulting solution; and recovering the solid;
    wherein said Fesoterodine fumarate does not develop degradation impurities of formula (IV), in an amount greater than 0.1% after 90 days at 25 ° C. with a relative humidity of 60%:

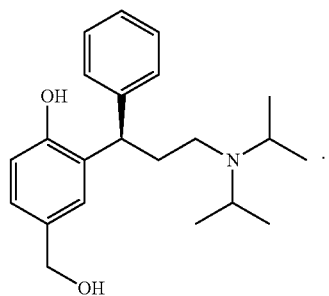

(IV)

2. Process according to claim 1 wherein the Fesoterodine base to fumaric acid molar ratio is comprised between about 1:0.5 and about 1:0.85.

3. The process according to claim 1, wherein when Fesoterodine base is crude Fesoterodine obtained from the acylation reaction between a compound of formula (IV)

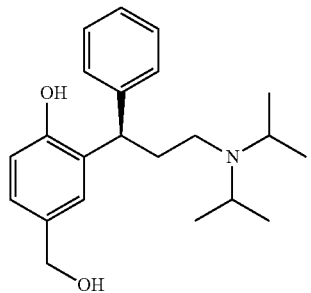

(IV)

with isobutyryl chloride, then the molar ratio of the compound of formula (IV) to fumaric acid is comprised between about 1:0.10 and about 1:0.85.

4. Process according to claim 3 wherein the molar ratio of the compound of formula (IV) to fumaric acid is comprised between about 1:0.4 and about 1:0.80.

5. A substantially stable to degradation Fesoterodine fumarate, wherein said Fesoterodine fumarate does not develop degradation impurities of formula (IV), in an amount greater than 0.1% after 90 days at 25 ° C. with a relative humidity of 60%:

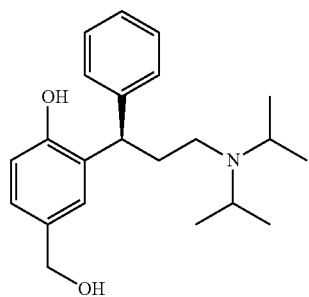
(IV)

wherein said Fesoterodine fumarate is obtained using a substoichiometic amount of fumaric acid.

6. The substantially stable to degradation Fesoterodine fumarate according to claim 5, wherein any degradation impurities of formulas (VI), (VII), (VIII) or (IX) are not increased after storage for 90 days at 25° C. and 60% relative humidity as compared to the degradation impurities of formulas (VI), (VII), (VIII) or (IX) before storage:

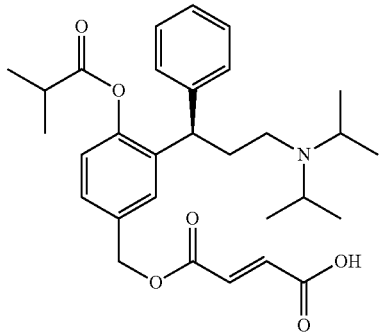
(VI)

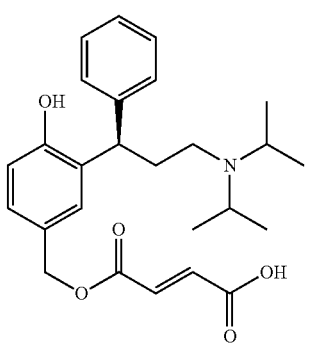
(VII)

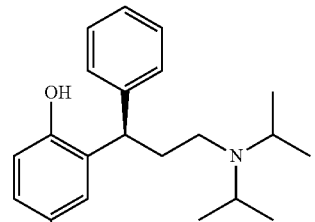
(VIII)

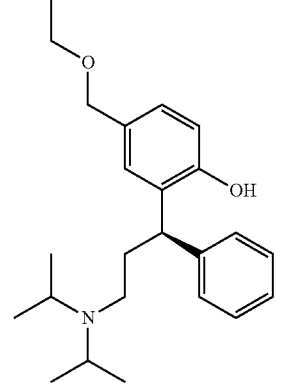

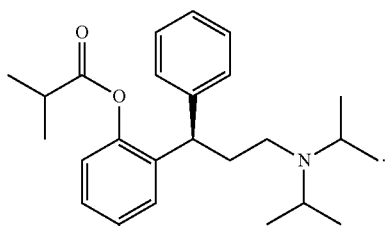
(IX)

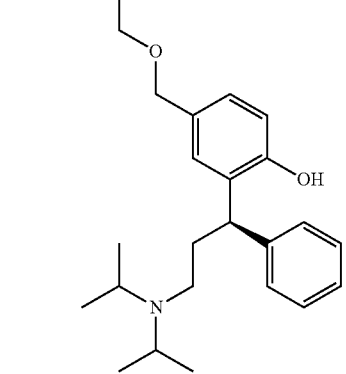

7. Fesoterodine fumarate according to claim 6, wherein said Fesoterodine fumarate has a total combined content of any impurities of formula (VI), (VII) (VIII) and (IX) equal to or lower than 0.1% after 90 days at 25° C. and 60% relative humidity, calculated as Area % by HPLC.

8. A pharmaceutical composition comprising substantially stable to degradation Fesoterodine fumarate according to claim 5 and a pharmaceutically acceptable carrier and/or excipient.

9. A substantially stable to degradation Fesoterodine fumarate according to claim 5, in combination with a carrier and/or excipient suitable for treatment of urinary incontinence in a mammal in need thereof.

10. The Fesoterodine fumarate according to claim 7, wherein the total content of the impurities of formula (VI), (VII) (VIII) and (IX) is between about 0.1% and about 0.01%, calculated as Area % by HPLC.

* * * * *